United States Patent [19]

Mori et al.

[11] Patent Number: 4,691,018

[45] Date of Patent: Sep. 1, 1987

[54] PYRIDINE DERIVATIVES AND THEIR USE AS ANTI-ALLERGIC AGENTS

[75] Inventors: Takashi Mori; Nobuhiro Ohi; Yoshiyuki Ohsugi; Yasuhiro Yamashita, all of Tokyo, Japan

[73] Assignee: Chugai Seiyaku Kabushiki Kaisha, Tokyo, Japan

[21] Appl. No.: 860,211

[22] Filed: May 6, 1986

[30] Foreign Application Priority Data

May 23, 1985 [JP] Japan .................................. 60-110642

[51] Int. Cl.$^4$ ........................................... C07D 213/60
[52] U.S. Cl. ..................................... 546/309; 546/323
[58] Field of Search ............................... 546/309, 323

[56] References Cited

FOREIGN PATENT DOCUMENTS 58-159465  3/1983  Japan .................................. 546/309
58-105920  4/1983  Japan .................................. 546/309

OTHER PUBLICATIONS

Introduction to Org. Chem., 2nd Ed., pp. 514–515.

Primary Examiner—Henry R. Jiles
Assistant Examiner—J. Richter
Attorney, Agent, or Firm—Browdy and Neimark

[57] ABSTRACT

A compound of the formula

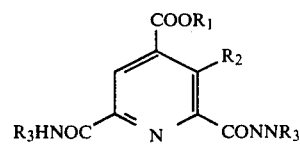

wherein $R_1$ is a hydrogen atom or a lower alkyl group which may be substituted with hydroxy, lower alkyl or di-lower alkylamino; $R_2$ is a hydrogen atom, an amino group or a lower alkylamino group; and $R_3$ is a lower alkyl group, and a non-toxic salt thereof, and a process for preparing the same are disclosed.

The compound and the salts thereof exhibit anti-allergic effects by the two different mechanisms and are expected to be useful as drugs for treating allergic diseases such as asthma, pollen allergy, atopic dermatitis and the like.

6 Claims, No Drawings

PYRIDINE DERIVATIVES AND THEIR USE AS ANTI-ALLERGIC AGENTS

This invention relates to pyridine derivatives represented by the Formula (I) and non-toxic salts thereof

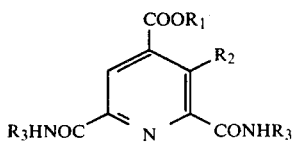
(I)

wherein $R_1$ is a hydrogen atom or a lower alkyl group which may be substituted with hydroxy, lower alkoxy or di-lower alkylamino; $R_2$ is a hydrogen atom, an amino group, or a lower alkylamino group; and $R_3$ is a lower alkyl group.

These derivatives and non-toxic salts thereof exhibit antiallergic effects and are useful as a drug for treating allergic diseases such as asthma, pollen allergy, atopic dermatitis and the like.

2,6-Bis(N-lower alkylcarbamoyl)pyridine-4-carboxylic acid derivatives represented by the Formula (I) have not been disclosed in the prior art references, and are novel. 2,6-Bis(N-lower alkylcarbamoyl)pyridine derivatives which are analogous to those of this invention are disclosed as an anti-cancer drug in Japanese Patent Public Disclosures Nos. 105920/83 and 159465/83. However, these references do not teach or suggest that this type of pyridine derivatives have the antiallergic effects.

On the other hand, it is understood that IgE antibody plays an important role in patients suffering from allergic diseases such as asthma, pollen allergy, atopic dermatitis or the like, and that an unusually high level of IgE in blood is often observed in patients having such a disease.

The inventors have studied many compounds in terms of their activity to selectively suppress the IgE antibody production, and found that, when tests were conducted using test animals in which the IgE antibody production ability was unusually accelerated, compounds of this invention showed selective suppression the IgE antibody production even at a low administration level. Furthermore, the inventors found the fact that the compounds of this invention had also the effect to suppress at a low concentration the release of chemical mediators such as histamine, SRS-A, etc. from mast cells, which was caused by the reaction of the IgE antibody with the corresponding antigen. Thus, the inventors discovered that the compounds of this invention simultaneously exhibited both of the two useful actions described above, so they continued their studies and finally completed this invention.

In the definition of substituents given for the Formula (I), "a lower alkyl group" means a linear- or branched-chain alkyl group having 1 to 4 carbon atoms, such as methyl, ethyl, n-propyl, iso-propyl, n-butyl, iso-butyl and the like. If the lower alkyl group is one for $R_1$, it may be substituted at any position with a hydroxy group, a lower alkoxy group or di-lower alkylamino group.

Similarly, "a lower alkoxy group" means an alkoxy group, the alkyl moiety of which was the same meaning as the lower alkyl group defined above.

The term "a lower alkylamino group" includes mono-and di-alkyl amino groups.

The compounds represented by the Formula (I) are novel as described above, and can be prepared as shown in the following scheme by reacting a compound of the Formula (II) with a lower alkylamine, and optionally hydrolyzing by the conventional method the ester group at 4-position of the compound of (Ia).

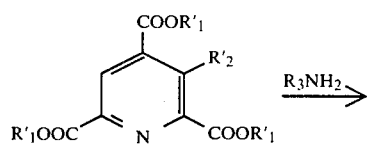
(II)

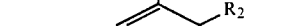
(Ia)

(Ib)

wherein $R'_1$ is the same as $R_1$ except that a hydrogen atom is not included, $R'_2$ is the same as $R_2$ or a halogen atom, and $R_2$ and $R_3$ are the same as defined above. If necessary, the compound of (Ib) can be esterified at the carboxyl group at 4-position to introduce a different alkyl group.

This amide formation reaction is carried out using 2–20 moles of a primary amine represented by the formula $R_3NH_2$ per mole of the compound (II) in a solvent such as tetrahydrofuran, dioxane, acetonitrile or alcohol or the like at a temperature from 0 to 50° C. Alternatively, the compounds of this invention can be prepared by hydrolyzing the compounds of the Formula (Ib) by the conventional method.

If the compound of the Formula (I) where $R_2$ is a lower alkylamino group is desired, the compound of the Formula (III) can be reacted with a lower alkylamine to subject the compound (III) to amidation and simultaneously to convert the chlorine atom at 3-position into a lower alkylamino group.

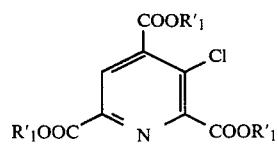
(III)

wherein $R'_1$ is the same as defined above.

This invention is further illustrated by the following Examples and Experiments.

EXPERIMENT 1

Inhibitory effect on passive cutaneous anaphylaxis (PCA)

Rat antiserum to egg albumin was prepared by the method of I. Mota, "Immunology" 7, 681–699 (1964), and 400 folds diluted. The diluted antiserum (0.1 ml) was injected into dorsal skin of rats (SD/JCL strain, male, 9-week-old) to subject them to passive immunization.

Forty-eight to seventy-two hours later, each rat was orally given a compound of this invention suspended in a 1% gum arabic aqueous solution. Five minutes after the administration, each rat was intravenously injected at its tail with 1 ml of a mixture containing equal volumes of a 0.5% solution of egg albumin in saline and 0.5% solution of Evans Blue in saline. Thirty minutes later, each rat was beheaded and the extravasated dye was quantitatively measured by the method of Katayama et al., "Microbiol. Immunol" 22, 89–101 (1978).

The percent inhibition was calculated by comparing the amount of Evans Blue leaking in the test groups with that in the control group in which a gum arabic aqueous solution containing no test compound was administered to the test animal.

The results are shown in Table 1. In Table 1, inhibition efficiencies of 30 to 50%, 51–70%, 71–90% and 91% or more are represented by the ratings +, ++, +++ and ++++, respectively. The numbers given to the test compounds correspond to the Example Nos.

TABLE 1

| Compound No. | Dose (mg/kg) | Percent Inhibition |
| --- | --- | --- |
| 1 | 5 | ++++ |
| 2 | 50 | + |
| 4 | 10 | ++ |
| 7 | 10 | ++ |
| 8 | 10 | ++ |
| 10 | 10 | +++ |
| 11 | 10 | ++++ |

EXPERIMENT 2

Inhibitory effect on production of IgE antibody SJL/J strain mice (8-week-old) were exposed to X-rays of 400 R, and concurrently injected intraperitoneally a mixture of 1 µg of Keyhole Limpet Hemocyanin (KLH) with 4 mg of an aluminum hydroxide gel. One week later, the mice were intraperitoneally administered with a mixture of 1 µg of dinitrophenyl group-binding KLH (DNP-KLH) with 4 mg of an aluminum hydroxide gel. From the next day of the immunization with DNP-KLH, each of the mice was forced to be orally administered by using gastric catherter with a test compound suspended in a 1% gum arabic aqueous solution. The mice in a control group were administered with only the gum arabic solution.

The serum was sampled from each of the mice treated above, and the amount of IgE therein was measured by the "Rat 48-hour PCA test" similarly as described in Experiment 1. The amount of IgE was expressed in terms of the maximum dilution of the serum by which a cutaneous reaction appeared in an area with a diameter of 5 mm or more to be observed.

The percent inhibition was indicated as the ratio of the amount of IgE of the test group to that of the control group.

The results are shown in Table 2 below. In Table 2, inhibition efficiencies of 25–50%, 50–75% and 75% or more are represented by ratings ++, +++ and ++++, respectively. The numbers given to the test compounds correspond to the Example Nos.

TABLE 2

| Compound No. | Dose (mg/kg) | Percent Inhibition |
| --- | --- | --- |
| 1 | 5 | ++++ |
| 2 | 50 | ++++ |
| 5 | 5 | +++ |
| 8 | 5 | ++ |
| 10 | 10 | ++++ |
| 11 | 5 | ++++ |

EXAMPLE 1

To a mixture of 16.8 g of tri-ethyl pyridine-2,4,6-tricarboxylate with 140 ml of tetrahydrofuran, was slowly added 11 g of a 40% methylamine aqueous solution followed by stirring the mixture overnight. After addition of acetic acid (9 g), the reaction mixture was evaporated under reduced pressure, and then water was added to the residue followed by extraction with chloroform. The organic layer was separated and evaporated to dryness, and the residue was purified by a column chromatography on silica gel. The product was recrystallized from a mixture of chloroform and hexane to give 8.9 g of ethyl 2,6-bis(N-methylcarbamoyl)pyridine-4-carboxylate. m.p. 183°–184° C.

NMR spectrum (CDCl$_3$)δ: 8.86(2H,s), 8.40(2H,d), 4.42(2H,q), 2.98(6H,d), 1.40(3H,t)

EXAMPLE 2

Methanol (20 ml) was added to 4.5 g of ethyl 2,6-bis(N-methylcarbamoyl)pyridine-4-carboxylate prepared by Example 1, and to the mixture was added a solution of 0.9 g of sodium hydroxide in 20 ml of water while stirring. The mixture was warmed to 50°–60° C. and, after addition of 250 ml of water, a small amount of the insoluble materials was removed by filtration.

Diluted hydrochloric acid was added to the filtrate to adjust its pH to 5, and after heating to 90°–100° C., the additional diluted hydrochloric acid was slowly added, thereby lowering its pH to 2–3. The mixture was allowed to cool, the solid was recovered by filtration and washed with water to give 3.5 g of 2,6-bis(N-methylcarbamoyl)pyridine-4-carboxylic acid. m.p. <300° C.

NMR spectrum (DMSO-d$_6$)δ: 9.34(2H,d), 8.57(2H,s), 2.97(6H,d)

EXAMPLE 3

2,6-Bis(N-methylcarbamoyl)pyridine-4-carboxylic acid (1 g) was mixed with methanol (50 ml), and to the mixture was added thionyl chloride (2 ml). After addition of thionyl chloride, the mixture was stirred at room temperature overnight. The mixture was then evaporated under reduced pressure, and water was added to the residue followed by extraction with chloroform. The organic layer was washed with a saturated sodium bicarbonate aqueous solution, and evaporated to dryness. The residual crystals were recrystallized from toluene to give 0.4 g of methyl 2,6-bis(N-methylcarbamoyl)pyridine-4-carboxylate. m.p. 202°–203° C.

NMR spectrum (CDCl$_3$)δ: 8.81(2H,s), 8.18(2H,d), 3.93(3H,s), 2.98(6H,d)

EXAMPLES 4-7

By the procedure similar to that described in Example 1, the compounds listed in Table 3 were prepared.

TABLE 3

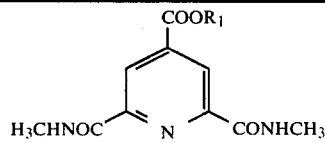

| Example No. | R₁ | m.p. (°C.) | recrystallization medium | NMR (δ) |
|---|---|---|---|---|
| 4 | n-propyl | 180–181 | chloroform/hexane | 8.81(2H,s), 8.35(2H,d), 4.30(2H,t), 2.98(6H,d), 1.5–2.1(4H,m), 1.00(3H,t) |
| 5 | iso-propyl | 183–184 | toluene | 8.82(2H,s), 8.08(2H,d), 5.28(1H,septet), 3.02(6H,d), 1.35(6H,d) |
| 6 | iso-butyl | 230–232 | chloroform/hexane | 8.80(2H,s), 8.15(2H,d), 4.12(2H,d), 2.96(6H,d), 1.7–2.5(1H,m), 1.00(6H,d) |
| 7 | 2-methoxy-ethyl | 194–195 | chloroform/hexane | 9.30(2H,d), 8.47(2H,s), 4.48(2H,m), 3.70(2H,m), 3.32(3H,s), 2.90(6H,d) |

EXAMPLE 8

2,6-Bis(N-methylcarbamoyl)pyridine-4-carboxylic acid (2.3 g) prepared in Example 2 was mixed with 50 ml of tetrahydrofuran and 3.1 g of ethylene glycol. After addition of 2.5 g of dicyclohexyl carbodiimide, the mixture was stirred at room temperature overnight. The mixture was then evaporated and the residue was purified by a column chromatography on silica gel, and recrystallized from dimethylformamide/benzene to give 0.3 g of 2-hydroxyethyl 2,6-bis(N-methylcarbamoyl)pyridine-4-carboxylate. m.p. 214°–215° C.

NMR spectrum (DMSO-d₆)δ: 9.32(2H,d), 8,48(2H,s), 4.98(1H,t), 4.37(2H,m), 3.77(2H,m), 2.90(6H,d)

EXAMPLE 9

Triethyl pyridine-2,4,6-tri-carboxylate was used as the starting compound and reacted with ethylamine and then with a sodium hydroxide aqueous solution in the manner described in Examples 1 and 2 to give 2,6-bis(N-ethylcarbamoyl)pyridine-4-carboxylic acid. Yield: 39%, m.p. 278°–280° C. (recrystallized from tetrahydrofuran/benzene).

EXAMPLE 10

To a solution of 7.5 g of triethyl 3-aminopyridine-2,4,6-tricarboxylate in 100 ml of tetrahydrofuran and 100 ml of ethanol, a 40% methylamine aqueous solution in a total amount of 30 g was added at room temperature 3 times every other day. Four days after the reaction was initiated, acetic acid (25 g) was added to the reaction mixture followed by evaporating it under reduced pressure. Water was added to the residue and extracted with chloroform. The organic layer was dried over sodium sulfate and evaporated to dryness The residue was purified by column chromatography on silica gel and recrystallized from toluene to give 3.5 g of ethyl 3-amino-2,6-bis(N-methylcarbamoyl)pyridine-4-carboxylate m.p. 185°–186° C.

NMR spectrum (CDCl₃)δ: 7.8–9.2(5H ), 4.34(2H,q), 2.92(6H,dd), 1.33(3H,t)

EXAMPLE 11

Triethyl 3-chloropyridine-2,4,6-tricarboxylate was reacted with methylamine as in Example 10 to give ethyl 3-methylamino-2,6-bis(N-methylcarbamoyl)pyridine-4-carboxylate. Yield: 51%, m.p. 169°–170° C. (recrystallized from toluene).

NMR spectrum (CDCl₃)δ: 9.59(2H,d), 8.60(2H,d), 8.1–8.5(2H), 4.32(2H,q), 2.7–3.1(9H,m), 1.33(3H,t)

EXAMPLE 12

Dimethylaminoethyl chloride (1.2 g) was added to a mixture of 2,6-bis(N-methylcarbamoyl)pyridine-4-carboxylic acid (2.37 g) with isopropyl alcohol (30 ml) followed by refluxing under stirring for 2 days. After allowing the mixture to cool, the resulting crystals were recovered by filtration, and recrystallized from methanol/benzene to give 0.5 g of 2-dimethylamino ethyl 2,6-bis(N-methylcarbamoyl)pyridine-4-carboxylate hydrochloride. m.p. 240°–242° C. (decomposition).

NMR spectrum (DMSO-d₆)δ: 9.66(2H,d), 8.64(2H,s), 4.78(2H,m), 3.60(2H,m), 2.90(12H)

What is claimed is:

1. A compound of the formula

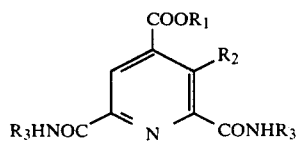

wherein R₁ is a hydrogen atom or a lower alkyl group which may be substituted with hydroxy, lower alkoxy or di-lower alkylamino; R₂ is a hydrogen atom, an amino group or a lower alkylamino group; and R₃ is a lower alkyl group, and a nontoxic salt thereof.

2. A compound of claim 1 wherein R₁ is a hydrogen atom.

3. A compound of claim 1 wherein R₁ is an alkyl group having 1–4 carbon atoms.

4. A compound of claim 1 wherein R₁ is an alkyl group having 1–4 carbon atoms and substituted with hydroxy, alkoxy having 1–4 carbon atoms or dialkylamino each of the alkyl moieties of which has 1 to 4 carbon atoms.

5. A compound in accordance with claim 1 wherein R₂ is a hydrogen atom.

6. A compound in accordance with claim 1 wherein R₂ is amino or lower alkylamino.

* * * * *